(12) United States Patent
Humphrey et al.

(10) Patent No.: US 6,489,471 B1
(45) Date of Patent: Dec. 3, 2002

(54) PROCESS FOR THE SYNTHESIS OF CARBAPENEM INTERMEDIATES, AND COMPOUNDS PRODUCED

(75) Inventors: Guy R. Humphrey, Hillsborough; Ross A. Miller, Fanwood; Nobuyoshi Yasuda, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/719,503

(22) PCT Filed: Jun. 11, 1999

(86) PCT No.: PCT/US99/13263
§ 371 (c)(1),
(2), (4) Date: Mar. 5, 2001

(87) PCT Pub. No.: WO99/65921
PCT Pub. Date: Dec. 23, 1999

Related U.S. Application Data
(60) Provisional application No. 60/089,585, filed on Jun. 17, 1998.

(51) Int. Cl.[7] ............................................. C07D 477/14
(52) U.S. Cl. ..................................................... 540/302
(58) Field of Search ........................................ 540/302

(56) References Cited

U.S. PATENT DOCUMENTS

| | | |
|---|---|---|
| 4,309,438 A | 1/1982 | Christiansen et al. |
| 4,479,947 A | 10/1984 | Christiansen |
| 4,994,568 A | 2/1991 | Christiansen |
| 5,034,384 A | 7/1991 | Greenlee et al. |
| 5,061,633 A * | 10/1991 | Meguro ............... 436/71 |
| 5,064,954 A | 11/1991 | Uyeo et al. |
| 5,478,820 A | 12/1995 | Betts et al. |
| 5,756,725 A | 5/1998 | Wilkening et al. |
| 5,990,101 A | 11/1999 | Aihara et al. |

FOREIGN PATENT DOCUMENTS

| | | |
|---|---|---|
| EP | 0 102 239 A1 | 3/1984 |
| EP | 0 212 404 A1 | 3/1987 |
| EP | 0 330 108 A1 | 8/1989 |
| EP | 0 476 649 A2 | 3/1992 |
| EP | 0 695 753 A1 | 2/1996 |
| WO | WO 99/52908 | 10/1999 |

OTHER PUBLICATIONS

Schmitt et al., The Journal of Antibiotics, vol. 41, No. 6, pp. 780–787, 1988.
Yasuda et al., Tetrahedron Letters, vol. 40, No. 3, pp. 427–730, 1999.
Imuta et al., Chemical & Pharmaceutical Bulletin, vol. 39, No. 3, pp. 663–671.

* cited by examiner

*Primary Examiner*—Mark L. Berch
(74) *Attorney, Agent, or Firm*—Valerie J. Camara; Sylvia A. Ayler; Mark R. Daniel

(57) ABSTRACT

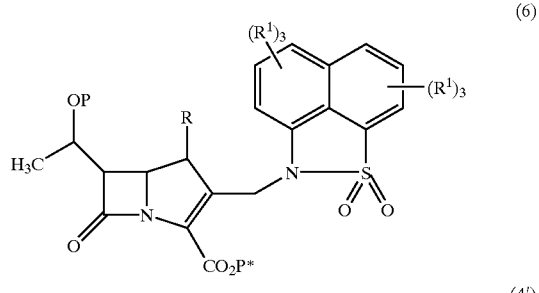

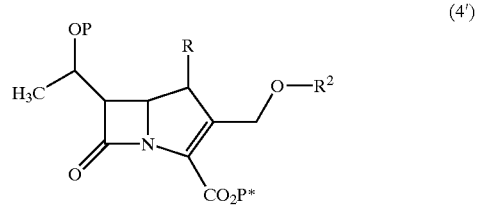

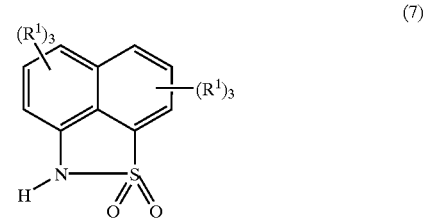

A process of synthesizing a carbapenem compound of formula (6) is disclosed, wherein R represents H or methyl, P and P* independently represent H or protecting groups and each $R^1$ is independently selected from: H, halo, OH, OP wherein P is a protecting group, $C_{1-6}$ alkyl or $C_{1-6}$ alkyl substituted with 1–3 of halo, OH, OP, $NH_2$, $NHC_{1-4}$ alkyl or $N(C_{1-4}$ alkyl$)_2$, comprising reacting a carbapenem of formula (4') with a compound of formula (7), wherein R, $R^1$, P and P* are as previously defined and $R^2$ represents acetate, C(O)OR' or P(O)(OR")$_2$, wherein R' and R" independently represent Clot alkyl, benzyl or aryl, in the presence of a catalyst to produce a compound of formula (6).

27 Claims, No Drawings

PROCESS FOR THE SYNTHESIS OF CARBAPENEM INTERMEDIATES, AND COMPOUNDS PRODUCED

"This application claims the benefit of U.S. Provisional Application No. 60/089,585, filed Jun. 17, 1998."

BACKGROUND OF THE INVENTION

The present invention relates to a process for synthesizing carbapenem intermediates and compounds produced. Generally hydroxymethylcarbapenems are substituted at the 2-position through a $CH_2$ link with various sidechains to prepare anti-methicillin resistant *Staphylococcus aureus* (MRSA) compounds. The intermediate compounds are included as well. Examples of carbapenems which are substituted with a naphthosultam-containing side chain at the 2-position are found in Schmitt, S. M. et al., *J. Antibiotics* 41(6): 780–787 (1988) and U.S. Pat. No. 5,756,725, issued May 26, 1998, the teachings of which are hereby incorporated by reference. European applications 0330108, 0102239, 0212404, 0695753 and 0476649 also disclose methods for synthesizing various antibiotic derivatives.

Many of the carbapenems are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). These antibacterials thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

In one aspect of the invention, a process of synthesizing a carbapenem compound of formula 6:

is disclosed wherein:

R represents H or methyl,

P* represents H, negative charge, or a carboxy protecting group;

P represents hydrogen, hydroxyl, or hydroxy-protecting group; and each $R^1$ is independently selected from: —R*; —Q; hydrogen; halo; —CN; —NO$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^h$; —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{3-7}$ cycloalkyl, unsubstituted or substituted with one to four R$^d$ groups;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

or R$^b$ and R$^c$ taken together with any intervening atoms represent a 4–6 membered saturated ring optionally interrupted by one to three of O, S, NR$^a$, with R$^a$ as defined above, or —C(O)—, said ring being unsubstituted or substituted with one to four R$^i$ groups;

each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$ONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —R* or—Q;

R$^e$, R$^f$ and R$^g$ represent hydrogen; —R*; —C$_{1-6}$ straight- or branched-chain alkyl unsubstituted or substituted with one to four R$^i$ groups;

or R$^e$ and R$^f$ taken together with any intervening atoms represent a 4–6 membered saturated ring optionally interrupted by one to three of O, S, —C(O)—or NR$^g$ with R$^g$ as defined above, said ring being unsubstituted or substituted with one to four R$^i$ groups;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

each R$^h$ independently represents hydrogen, a —C$_{1-6}$ straight or branched-chain alkyl group, a —C$_{3-6}$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

Q is selected from the group consisting of:

wherein:

a and b are 1, 2 or 3;

L– is a pharmaceutically acceptable counterion;

α represents O, S or NR$^s$;

β, δ, λ, μ and σ represent CR$^t$, N or N$^+$R$^s$, provided that no more than one of β, δ, λ, μ and σ is N$^+$R$^s$;

3

R* is selected from the group consisting of:

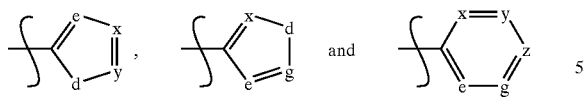

wherein:
d represents O, S or $NR^k$;
e, g, x, y and z represent $CR^m$, N or $N^+R^k$, provided that no more than one of e, g, x, y and z in any given structure represents $N^+R^k$;
$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;
each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^hCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;
$R^n$ and $R^o$ represent hydrogen, phenyl; —$C_{1-6}$ straight- or branched-chain alkyl unsubstituted or substituted with one to four $R^i$ groups;
each $R^s$ independently represents hydrogen; phenyl or —$C_{1-6}$ straight- or branched-chain alkyl, unsubstituted or substituted with one to four $R^i$ groups;
each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;
$R^u$ and $R^v$ represent hydrogen or —$C_{1-6}$ straight- or branched-chain alkyl, unsubstituted or substituted with one to four $R^i$ groups;
or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;
each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;
or $R^h$ and $R^w$ taken together with any intervening atoms represent a 5–6 membered saturated ring, optionally interrupted by one or two of O, S, $SO_2$, NH or $NCH_3$;
$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)$

4

$NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;
$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;
or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups,
and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups;
comprising reacting a carbapenem of formula 4':

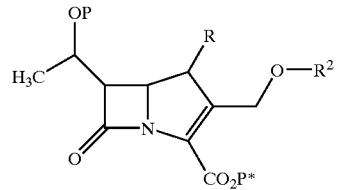

with a compound of formula 7:

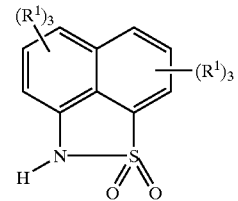

wherein R, $R^1$, P and P* are as previously defined and $R^2$ represents C(O)OR', C(O)R' or $P(O)(OR'')_2$, wherein R' and R'' independently represent $C_{1-6}$ alkyl, aryl or benzyl, in the presence of a catalyst to produce a compound of formula 6.

In another aspect of the invention there is disclosed a compound of formula 4

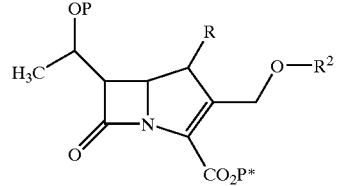

or a pharmaceutically acceptable salt thereof;
wherein P, P*, and R are described above and $R^2$ is C(O)R' or C(O)OR', wherein R' represents $C_{1-6}$ alkyl, aryl or benzyl.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

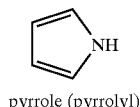
pyrrole (pyrrolyl)

imidazole (imidazolyl)

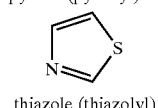
thiazole (thiazolyl)

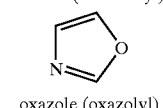
oxazole (oxazolyl)

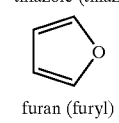
furan (furyl)

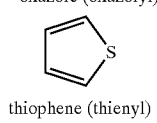
thiophene (thienyl)

-continued

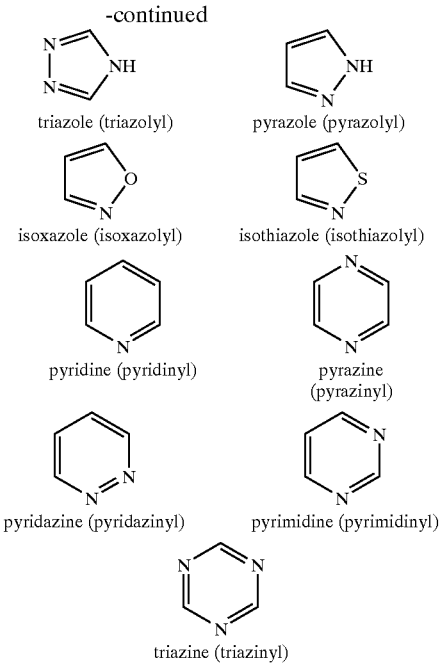

Heteroaryliulm refers to heteroaryl groups bearing a quaternary nitrogen atom and thus a positive charge. Examples include the following:

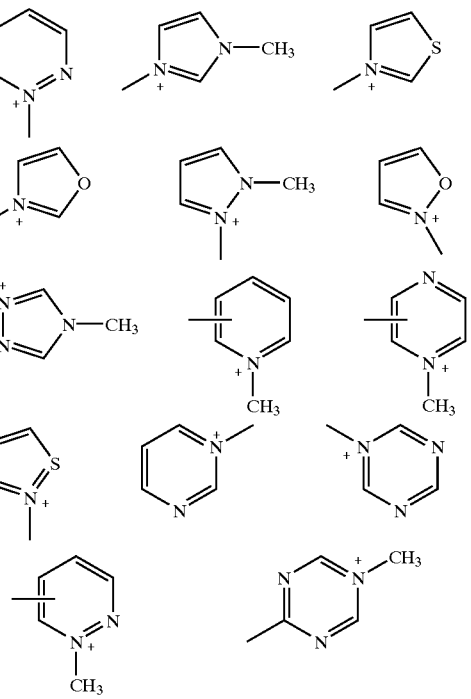

When a charge is shown on a particular nitrogen atom in a ring which contains one or more additional nitrogen atoms, it is understood that the charge may reside on a different nitrogen atom in the ring by virtue of charge resonance that occurs.

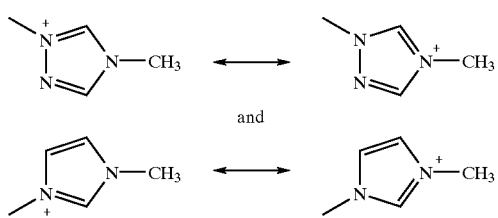

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "protected", such as by P, P* and the like, this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the compounds of the present invention, P and P* represent hydroxyl and carboxyl protecting groups, respectively. These groups are generally removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups P* include allyl, benzhydryl, 2-naphthylmethyl, benzyl, silyl groups such as t-butyldimethylsilyl (TBDMS), trimethylsilyl, (TMS), triethylsilyl (TES), and trimethylsilylethyl, phenacyl, p-methoxybenzyl, o-nitrobenzyl, p-methoxyphenyl, p-nitrobenzyl, 4-pyridylmethyl, 2,2,2-trichloroethyl, and t-butyl.

Examples of suitable hydroxy protecting groups P include TMS, TES, TBDMS, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

With respect to —$CO_2$P*, which is attached to the carbapenem nucleus at position 3, this can represent a carboxylic acid group (P* represents H), a carboxylate anion (P* represents a negative charge), a pharmaceutically acceptable ester (P* represents an ester forming group) or a carboxylic acid protected by a protecting group (P* represents a carboxyl protecting group). The pharmaceutically acceptable salts referred to above may take the form —COO P*, where P* is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include phosphate, sulfate and acid addition salts. Thus, the Formula 4 compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, phosphate, sulfate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

A base can optionally be added to the process. Suitable bases include trialkylamines such as triethylamine, trimethylamine, ethyldimethylamine, tri-n-propylamine and the like, 1,8-diazabicyclo[5.4.0.]undec-7-ene (DBU), pyridine, lutidine, collidine, 4-dimethylaminomethylpyridine, inorganic carbonates and bicarbonates such as sodium carbonate, sodium bicarbonate, potassium bicarbonate, potassium carbonate, and the like and tartrates such as potassium sodium tartrate, potassium tartrate, potassium bitartrate, sodium tartrate, sodium bitartrate and the like. Preferable bases are pyridine, potassium sodium tartrate, sodium carbonate, sodium bicarbonate, potassium bicarbonate, or potassium carbonate.

Suitable catalyst are those which contain a palladium (Pd) source, preferably those which contain a palladium and a phosphine ligand source or a phosphite ligand source. Examples of a palladium sources $Pd(OAc)_2$, $Pd(PPh_3)_4PdCl_2$, $PdCl_2(PPh_3)_2$, $PdCl_2(CH_3CN)_2$ and $Pd_2DBA_3$, and the like, wherein DBA is dibenzylidene acetone. Examples of ligands are triphenylarsine, trifurylphosphine, trialkylphosphites ($P(OR^+)_3$; wherein $R^+$ is $C_{1-10}$ alkyl), such as triethylphosphite, tributylphosphite, trimethylphosphite, triisopropylphosphite and the like, triarylphosphite such as triphenylphosphite (referred to as $PPh_3$ or TPP) and the like, DPPE, DPPP, preferably triarylphosphite or trialkylphosphites and most preferably $C_{1-4}$ phosphite or $PPh_3$. Examples of catalysts containing ligands are $Pd(OAc)_2$/TPP, $Pd_2(DBA)_3$/TPP and the like.

The reaction is generally carried out using a solvent such as toluene, $C_{1-6}$ alcohols such as isopropyl alcohol, methanol, ethanol, hexanol, butanol, and the like, acetonitrile, tetrahydrofuran (THF), ether, ester such as ethyl acetate, isopropylacetate and the like, benzene, dimethylformamide, N-methylpyrolidinone, dimethylsulfoxide and the like or a combination of the above with water.

In particular, processes of interest are those described above wherein P represents a member selected from the group consisting of TMS, TES, TBDMS, trimethylsilylethyl, o-nitrobenzyloxycarbonyl, p-nitrobenzyloxycarbonyl, benzyloxycarbonyl, allyloxycarbonyl, t-butyloxycarbonyl, 2,2,2-trichlorethyl and 2,2,2-trichloroethyloxycarbonyl.

Other processes that are of particular interest are those described above wherein P* represents a member selected from the group consisting of: allyl, benzhydryl, 2-naphthylmethyl, benzyl, silyl groups such as t-butyldimethylsilyl (TBDMS), trimethylsilyl, (TMS), triethylsilyl (TES), trimethylsilylethyl, phenacyl, p-methoxybenzyl, o-nitrobenzyl, p-methoxyphenyl, p-nitrobenzyl (PNB), 4-pyridylmethyl, 2,2,2-trichlorethyl and t-butyl.

Still other processes that are of particular interest are those described above wherein R represents methyl.

Still other processes that are of particular interest are those described above wherein at least one $R^1$ represents a positive charged.

Still other processes that are of particular interest are those described above wherein $R^2$ represents C(O)OR' or P(O)(OR")$_2$ and most preferably C(O)OR'.

Still other processes that are of particular interest are those described above wherein R, P and P* are described above and one $R^1$ group represents a —$C_{1-6}$ straight or branched chain alkyl group, substituted with one to four $R^d$ groups, wherein one $R^d$ group represents —R* or Q;

In another embodiment of the invention a process for making a compound of formula 6:

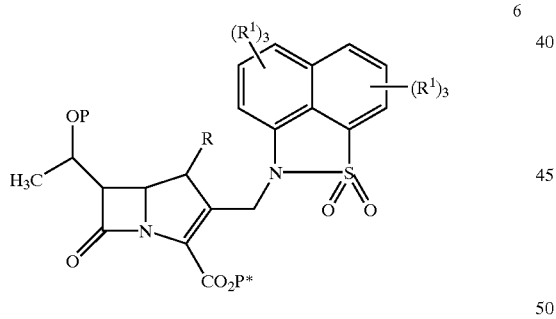

6 is disclosed wherein R, $R^1$, P and P* are described above; comprising

Step 1.
reacting a carbapenem of formula 3:

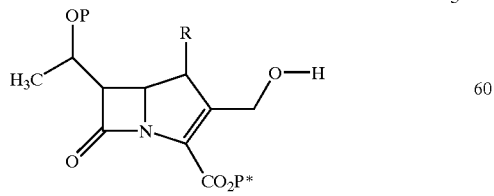

3 with an alkylhaloformate in the presence of a base to produce a compound of formula 4':

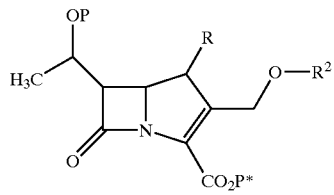

4'

Step 2.

reacting 4' with a compound of formula 7:

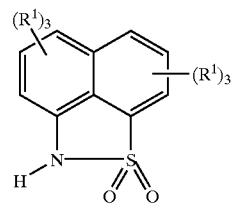

7 wherein R, $R^1$, P and P* are as previously defined and $R^2$ represents C(O)OR', C(O)R' or P(O)(OR")$_2$, wherein R' and R" independently represent $C_{1-6}$ alkyl, benzyl or aryl, in the presence of a catalyst to produce a compound of formula 6. Examples of alkylhaloformates are isobutylchloroformate, ethylchloroformate, methylchoroformate, propylchloroformate and the like, preferably isobutylchloroformate or ethylchloroformate. In another aspect of this invention a base, such as those previously mentioned, is optionally added to Step 2.

The process of the present invention is illustrated by the following generic scheme:

FLOW SHEET A

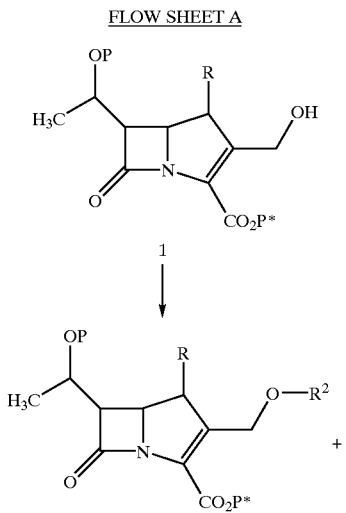

1

4'

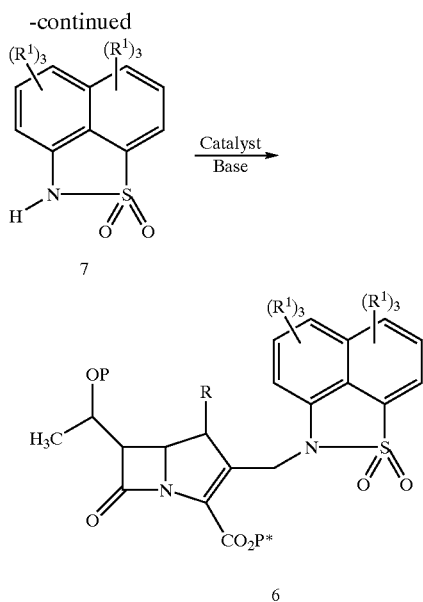

FLOW SHEET B

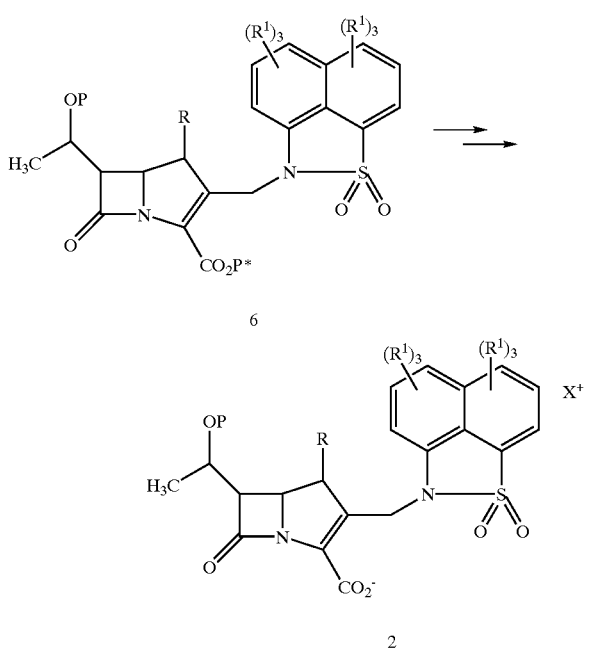

With reference to Flow Sheet A, the naphthosultam side chain group (SCG) 7 used in the synthesis of the compounds of the present invention have, in some cases, been described in the chemical literature. In other cases, precursor compounds which may be readily converted to the requisite naphthosultam have been described in the literature. In cases where the requisite naphthosultam is not known in the literature it is neceessary to synthesize the naphthosultam by a newly developed synthesis. One skilled in the art can adapt a previously published synthesis of an analogous naphthosultam to prepare the requisite compound in a straightforward manner without undue experimentation. Examples of naphthosultam synthesis are described herein (see below).

The naphthosultam side chain group (SCG) is initially reacted with a suitably protected carbapen-2-em-3-carboxylate 1 having an activated hydroxymethyl group at the 2-position.

The carbapenem nucleus 1 having a —CH$_2$OH substituent at position 2 can be obtained in accordance with Schmitt, S. M. et al., J. Antibiotics 41(6): 780–787 (1988). The compounds disclosed in U.S. Pat. No. 5,756,725, issued May 26, 1998 can also be prepared in accordance with the invention herein. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxycarbonyl, benzyloxycarbonyl, p-nitrobenzyloxycarbonyl, 2-trichloroethoxycarbonyl and the like.

The carbapenem 4' can be made in accordance with techniques such as those which are disclosed in U.S. Pat. Nos. 5,034,384, 4,994,568 and 5,478,820, herein incorporated by reference. For example, carbapenem 4' can be obtained by reacting carbapenem 1, wherein P is TES and P* is PNB, with a weak base such as pyridine in the presence of a solvent, and adding a $C_{1-6}$ alkylchloroformate such as isobutylchloroformate or ethylchloroformate. Preferred carabapenem compounds of 4' are those in which $R^2$ is an allylic $C_{1-6}$ carbonate, $C_{1-6}$ phosphate or ester such as acetate, most preferably an allyic $C_{1-6}$ carbonate.

In general, the addition of the naphthosultam side chain group 7 (SCG) to the carbapenem 4' is accomplished by reacting the carbapenem 4' with the naphthosultam side chain group 7 in a suitable solvent such as tetrahydrofuran (THF), ether, acetonitrile, a $C_{1-6}$ alcohol such as isopropanol, dimethylformamide (DMF), benzene, dimethylsulfoxide (DMSO), and the like, preferably acetonitrile or isopropanol, in the presence of a palladium catalyst sytem, described above, at a temperature between about 0° C. and 150° C., preferably about 15° C. to about 50 ° C., and most preferably about 20° C. to about 35° C., for about 5 to 90 minutes followed by an appropriate workup and isolation procedure familiar to those skilled in the art to yield the compounds of 6. A base, described above, can also be optionally added to the process.

The preferable palladium catalyst system is one which includes a ligand. Examples of such catalyst systems are Pd(OAc)$_2$/TPP, Pd$_2$(DBA)$_3$TPP, Pd(OAc)$_2$/triethylphosphite, Pd(OAc)$_2$/trifurylphosphine, Pd$_2$(DBA)$_3$/trifurylphosphine, Pd$_2$(DBA)$_3$/triethylphosphite and the like, with an optimal palladium level of about 0.1 mole % to about 15 mole %, preferably about 0.5 mole % to about 2 mole % and an optimal ligand level of about 0.3 mole % to about 45 mole %, preferably about 6 to about 11 mole %.

In the case where a trialkylphosphite such as triethylphosphite, triarylphosphite such as triphenylphosphite or triarylphosphine such as trifurylphosphine ligand is employed it is preferred that the temperature range is about 20° C. to about 35° C., which allows for direct coupling of a charged (i.e., at least one $R^1$ is charged) substituted naphthosultam to the carbapenem carbonate.

With reference to Flow Sheet B, the compounds of 2 can be prepared by modifying the naphthosultam side chain of 6 as desired, and then removing any protecting groups which are present to afford the desired final product as taught in U.S. Pat. No. 5,756,725, herein incorporated by reference.

To obtain the compounds disclosed in U.S. Pat. No. 5,756,725, modification of the naphthosultam side chain of compounds 6, which is generally necessary to introduce the charged substituent of 2, is best accomplished before removal of the protecting groups. For compounds which contain a hydroxyl group in the side chain, i.e. in $R^1$, a positively charged substituent may be introduced into the side chain by first activating the hydroxyl group by converting it to a suitable leaving group such as a triflate, mesylate, tosylate, iodide, chloride, bromide, and the like, and then displacing the resulting leaving group with a compound Q*, such as N-methyl-imidazole, N-(2-hydroxyethyl)-imidazole, N-methyl-diazabicyclooctane, 1-(carbamoylmethyl)-4-aza-1-azoniabicyclo-[2.2.2.]-octane, 1-(3-hydroxyprop-1-yl)-4-aza-1-azoniabicyclo-[2.2.2.]-octane, pyridine, morpholine and the like which contains a nitrogen atom that can act as a nucleophile.

Alternatively, in some cases, the charged substituent may be incorporated in the naphthosultam side chain before addition of the naphthosultam to the carbapenem, which is preferred when a trialkylphosphite or triarylphosphite ligand is employed in the catalyst system. Alternatively, the charged substituent may be introduced after deprotection of 6. However, introduction of the charged substituent by modification of 6 before deprotection is greatly preferred.

In some cases, activation of the hydroxyl group and displacement by Q* to produce 2 may be accomplished in a single step by taking advantage of the basic character of compound Q* and using it as a base in the activation reaction.

The conversion of the hydroxyl group to a suitable leaving group is accomplished by treating the hydroxyl substituted compound in a suitable solvent such as dichloromethane, dichloroethane, toluene, tetrahydrofuran, ether, acetonitrile, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, lutidine, diisopropylethylamine, and the like at a temperature of between about —100° C. and about 0° C. for about 5 to about 120 minutes. The intermediate thus obtained contains a leaving group, which may be converted to an alternative leaving group, iodide, by treating a solution of the intermediate in a suitable solvent such as acetone, methyl ethyl ketone, and the like at about –10° C. to about 50° C. with an excess of sodium iodide or potassium iodide for about 0.25 to about 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with reagent Q*. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO, and the like as described in the preceding paragraphs. The resulting activated intermediate is treated with 1–3 molar equivalents of compound Q* at a temperature of between about—78° C. and about 50° C. for about 15 to about 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q* is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q*. A silver salt of a non-nucleophilic acid, such as silver trifluoromethanesulfonate, silver tetrafluoroborate and the like is then added. Although the reaction will proceed in the absence of the silver salt, the reaction proceeds more rapidly in the presence of the silver salt. In addition, the silver salt assists in the removal of the displaced iodide from the reaction mixture which can improve the efficiency of subsequent steps. The resulting mixture is then subjected to a standard work-up procedure familiar to those skilled in the art to afford a crude product which is purified, if necessary, by recrystallization or chromatography.

An alternative method for introducing a positive charge into the side chain may be applied to side chains (i.e. $R^1$ groups) that contain a nitrogen atom which may be quaternized by reaction with a suitable alkylating reagent AR, such as methyl iodide, methyl bromide, benzyl trichloroacetimidate, bromoacetamide, chloroacetamide, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

By way of example, the conversion of the hydroxyl group to a suitable leaving group can be accomplished by triflation which can be carried out in dichloromethane, dichloroethane, toluene, and the like using lutidine as a base. An aqueous citric acid work-up can be used to remove the lutidine followed by a solvent switch into a solvent such as acetonitrile. The activated hydroxyl group is displaced by reacting the activated intermediate with a reagent Q* such as DABCO acetamide to yield a protected DABCO coupled product.

The synthesis of the target compound is completed by removing any protecting groups which are present in the penultimate intermediate using standard techniques which are well known to those skilled in the art. The hydroxy protected substituent can be deprotected by reacting the hydroxy protected penultimate intermediate with an acid such HCl, $H_2SO_4$, MsOH, TFA, $H_3PO_4$, TsOH and the like or fluoride anion such as TBAF, HF-pyridine, ammonium fluoridate and the like. The carboxy protected substituent can be deprotected by hydrogenolysis ($H_2$) in the presence of palladium on carbon, Raney Ni, Pd(OH)$_2$/carbon, palladium on $Al_2O_3$, platinum on carbon catalyst and the like followed by reduction with a metal such as zinc and photolysis (by photolysis methods known in the art). The deprotected final product is then purified, as necessary, using standard techniques such as ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

The compounds of the present invention are valuable intermediates for antibacterial agents, such as those described in U.S. Ser. No. 08/825,786, that are active against various Gram-positive and to a lesser extent Gram-negative bacteria, and accordingly find utility in human and veterinary medicine.

Many of the compounds that can be made in accordance with the present invention are biologically active against MRSA/MRCNS. In vitro antibacterial activity is predictive of in vivo activity when the compounds are administered to a mammal infected with a susceptible bacterial organism.

The invention is further described in connection with the following non-limiting examples.

PREPARATIVE EXAMPLE 1

Step 1 - Chlorosulfonation

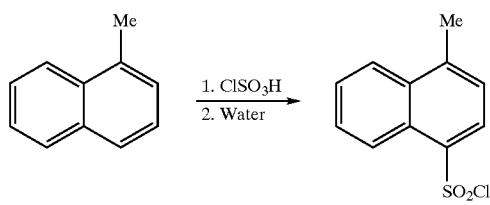

A three neck flask was charged with methylnaphthalene (2.63 Kg) and trifluoroacetic acid (13.2 L). The two-phase mixture was stirred and cooled to 5° C. using an ice-water bath. Chlorosulfonic acid (2.93 L) was added over 30 minutes maintaining the reaction temperature at <20° C. The reaction was quenched with deionized water at 10–20° C. over 15 min.

The product crystallized upon addition to water to give a white slurry.

The reaction vessel was washed with TFA/water (1:1, 1.0 L) and the wash added to the quench vessel. The cake was filtered on a polypropylene filter cloth and washed with water. The cake was dried in nitrogen stream overnight.

Step 2 - Sulfonamide

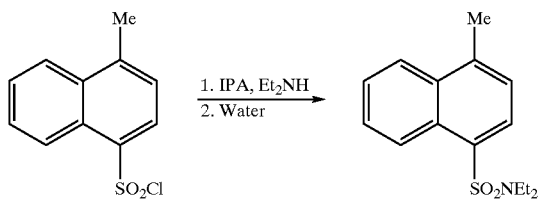

A flask was charged with methylnaphthalenesulfonyl chloride (4.0 Kg) and isopopanol (12.0 L). Diethylamine (3.73 L) was added to the slurry over 10 min.

An exotherm to about 65° C. occured and the starting material dissolved. The reaction progress was monitored by HPLC.

The solution was cooled to 20° C. and water (4 L) added. The mixture was seeded with sulfonamide product (2 gm) and aged at 20° C. for 20 min. The remaining water (32 L) was added over 1 h. The resultant slurry was aged at 20° C. for 20 min.

The slurry was filtered on a 23" polypropylene filter cloth and washed with water (12 L). The cake was dried in nitrogen stream overnight.

Step 3 - Nitration

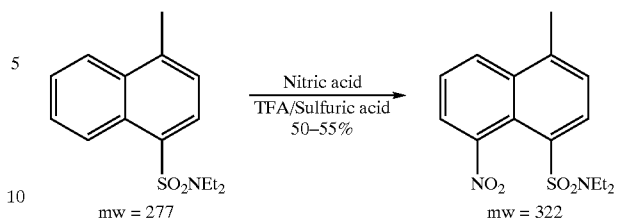

A 2 L flask, fitted with nitrogen inlet, mechanical stirrer, addition funnel and temperature probe was charged with N,N-Diethyl-1-Methyl-4-naphthalenesulfonamide (30 gms) and trifluoroacetic acid (TFA) (150 mL). The resultant solution was cooled to 15° C. Concentrated sulfuric acid (30 mL) was added over 2 minutes. The solution was cooled to −3° C.

Fuming nitric acid (6.2 mL) was added to the solution with rapid stirring over about 30 min maintaining the reaction temperature at −3 to +5° C.

The reaction progress was monitored by HPLC. The reaction was considered complete when <1% starting material remained by HPLC analysis (by area relative to product at 200 nm).

Water (375 mL) was added to the solution over 60 min. maintaining the quench temperature less than 25° C. using ice-water bath. The resultant slurry was aged at 20° C. for 30 min, filtered and the cake washed with water (100 mL).

The cake was dried in a nitrogen stream until the residual water content was <35% w/w.

The partially dried solid was slurried in ethyl acetate (75 mL) at 30° C. for 30 min. Hexane (150 mL) was added over 20 min and the slurry aged at 20° C. for 30 min. The slurry was filtered, washed with hexane (100 mL) and dried in a nitrogen stream overnight.

Step 4 - Reduction-Cyclization

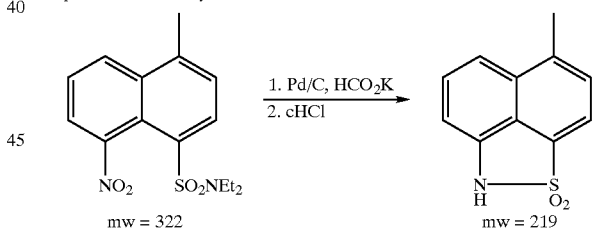

A 72 L round bottom flask was equipped with a $N_2$ inlet, thermocouple, and an overhead stirrer. The flask was charged with 2.20 Kg of 1-methyl-4-diethylsulfonamide-5-nitronaphthalene, along with ethanol (20 L).

Pd/C 10 wt% (50 wt % water wet, 0.17 Kg) was charged as a slurry in water (800 ml) and rinsed down with water (80 ml) and ethanol (6 L). To the resultant slurry was added potassium formate (1.74 Kg) in one portion. The slurry was warmed to 60° C. for 1 h then to reflux for 1 h.

The reaction was considered complete when <0.2% SM remained relative to the starting material as determined by HPLC.

On complete reaction the mixture was cooled to 20° C. and concentrated hydrochloric acid (2.73 L) added over about 20 min.

The resultant slurry was filtered through a pad of solka-floc™ and the cake washed with 10% hydrochloric acid in ethanol (total of 13 L). The combined filtrates were recharged to the cleaned 72 L flask and heated to reflux (81° C.) for 3–4 h to achieve complete cyclization.

The solution was cooled to 40° C. and concentrated to a slurry. The slurry was cooled to 20° C. and water (7.5 L) added over 30 min. The slurry was cooled to 5° C. and aged for 15 min.

The slurry was filtered and washed with water (5 L). The crystalline solid was dried under a stream of nitrogen overnight.

Step 5 - Dilithiation-carboxylation

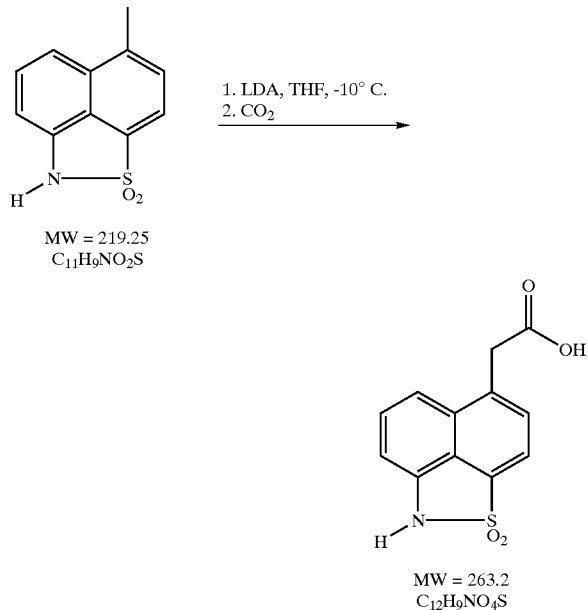

Step 6 - Borane reduction

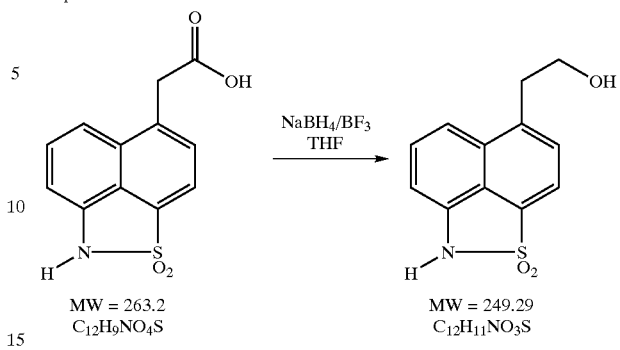

A 50 L round bottom flask was set up and equipped with a $N_2$ inlet, thermocouple, addition funnel and an overhead stirrer. The flask was charged with dried NH-sultam carboxylic acid (1.14 Kg) and THF (18 L). The slurry was cooled to 15° C. To this slurry was added $NaBH_4$ (327 g), followed by the slow addition of $BF_3$ etherate (1.42 L).

The slurry was aged at 15–20° C. and the reaction progress monitored by HPLC.

The slurry was cooled to 10° C. and methanol (1.2 L) slowly added to quench excess borane. 2N HCl (11 L) was added slowly and aged for 30 min. The quenched reaction mixture was distilled at atmospheric pressure to remove volatiles. The resultant solution was cooled to 55° C., seeded to initiate crystallization and cooled to 15° C. over 1 h. After aging for 30 min, the slurry was filtered, washed with 10 L water and dried under a stream of nitrogen.

Step 7—Dilithiation-Hydroxymethylation

A 10 mL flask equipped with nitrogen inlet, stirrer, and temperature probe was charged with THF (2 mL).

Diisopropylamine(0.14 mL) was added. The solution was cooled to −15° C. and n-butyllithium (0.66 mL) added dropwise maintaining the reaction temperature between −15° C. and 0° C. to produce lithium diisopropylamide (LDA).

A separate 20 mL flask equipped with stirrer and nitrogen inlet was charged with THF (2 mL) and 1-Me NH naphthosultam (0.07 gm). The solution was degassed by vacuum/purging with nitrogen and cooled to −15° C. and the LDA solution added dropwise keeping the solution temperature between −15° C. and −5° C. to produce the dianion solution.

The dianion solution was aged for 30 min at −15° C.

A separate 20 mL flask with stirrer, nitrogen inlet and temperature probe was charged with THF (2 mL) and para formaldehyde (0.12 gm) and degassed with a vacuum /nitrogen purge. The solution was cooled to −20° C. The dianion solution was then slowly added to this parafomaldehyde solution while ensuring efficient mixing. After warming to 10° C., 10 mL of 2N HCl was added the solution and was aged for 30 min.

The solution was concentrated atmospherically to about 10 mL to remove THF and initiate crystallization. The resultant slurry was aged at 15° C. for 30 min, filtered and the cake washed with water(10 mL) and dried in a nitrogen stream.

A 20 L flask equipped with nitrogen inlet, stirrer, temperature probe and addition funnel was charged with THF (5 L). Diisopropylamine(1.34 L) was added. The solution was cooled to −15° C. and n-butyllithium (6.0 L) added dropwise maintaining the reaction temperature between −15° C. and 0° C. to produce lithium diisopropylamide (LDA).

A separate 50 L flask equipped with stirrer and nitrogen inlet was charged with THF (10 L) and 1-Me NH naphthosultam (1.0 Kg). The solution was degassed by vacuum/purging with nitrogen and cooled to −15° C. and the LDA solution added dropwise keeping the solution temperature between −15° C. and −5° C to produce the dianion solution.

The dianion solution was aged for 30 min at −15° C.

A separate 100 L flask equipped with stirrer, nitrogen inlet and temperature probe was charged with THF (10 L) and degassed with a vacuum /nitrogen purge. The solution was cooled to −20° C. and bone-dry grade $CO_2$ bubbled into the THF until saturation was reached. The dianion solution was then slowly added to this carbonated solution while ensuring efficient mixing of the resulting slurry. After warming to 10° C., 10 L of 2N HCl was added the solution and was aged for 30 min.

The solution was concentrated atmospherically to about 10 L to remove THF and initiate crystallization. The resultant slurry was aged at 15° C. for 30 min, filtered and the cake washed with water(10 L) and dried in a nitrogen stream.

19

Preparation Example 2

Systhesis of 5-(2-(trimethylsilloxy)-ethyl)-1,8-naphtosultam

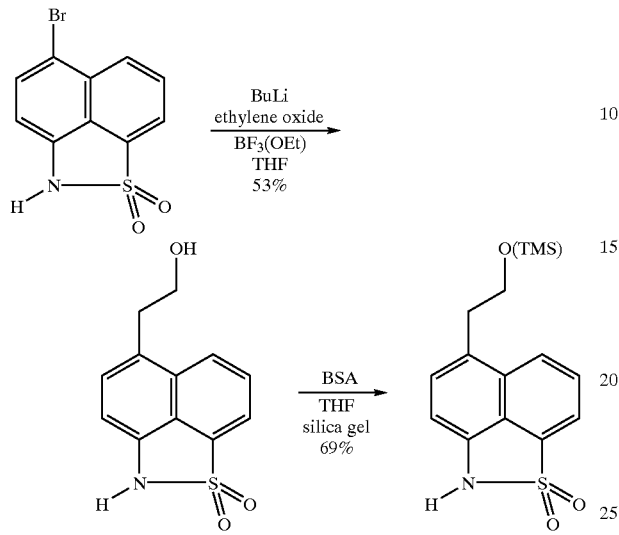

Step 1: 5-(2-(hydroxy)-ethyl)-1,8-naphthosultam

A solution of 5-bromo-1,8-naphthosultam (0.6 g, 2.11 mmol) in anhydrous tetrahydrofuran (10 mL) under nitrogen was cooled in a dry ice/ acetone bath. N-butyllithium (3.3 mL of a 1.6 M solution in hexanes, 5.28 mmol) was added over 7 minutes and the suspension was stirred an additional 8 minutes. An excess of ethylene oxide was slowly bubbled into the mixture over 5 minutes. Boron trifluoride etherate (0.26 mL, 2.11 mmol) was then added over 5 minutes. After an additional 20 minutes, the reaction was quenched with the addition of acetic acid (0.35 mL, 6 mmol). The mixture was partitioned between ethyl acetate (100 mL) and water (100 mL). The ethyl acetate layer was washed with saturated aqueous sodium chloride (50 mL), dried over magnesium sulfate, filtered, and evaporated. The residual oil (0.7 g) was dissolved in 5% methanol/methylene chloride and was loaded onto a 24×2.75 cm silica gel column (silica gel 60, packed/loaded/eluted with 5% methanol/methylene chloride), collecting 8 mL fractions. Fractions 26–39 were combined and evaporated to give the title compound as an oil (0.28 g). $^1$H NMR (DMSO-$d_6$, 500 MHz) δ3.22 (t, $CH_2Ar$), 3.87 (t, $CH_2OH$), 6.79 (d, ArH), 7.35 (d, ArH), 7.74 (t, ArH), 7.91 (d, ArH) and 8.21 (d, ArH).

Step 2: 5-(2-(trimethylsilyloxy)-ethyl)-1,8-naphthosultam

A solution of 5-(2-(hydroxy)-ethyl)-1,8-naphthosultam (0.09 g, 0.36 mmol) in tetrahydrofuran (1 mL) was treated with N,O-Bis(trimethylsilyl)acetamide (0.223 mL, 0.90 mmol). The mixture was stirred at room temperature for 20 minutes and was evaporated. The residual oil was dissolved in methylene chloride (3 mL) and was filtered through silica gel 60 (2.7 g), eluting the silica with additional methylene chloride (50 mL). The solvent was evaporated under vacuum and the residue was lyophilized from benzene (3 mL) to give the title compound as a white solid (0.08 g).

20

Example 1

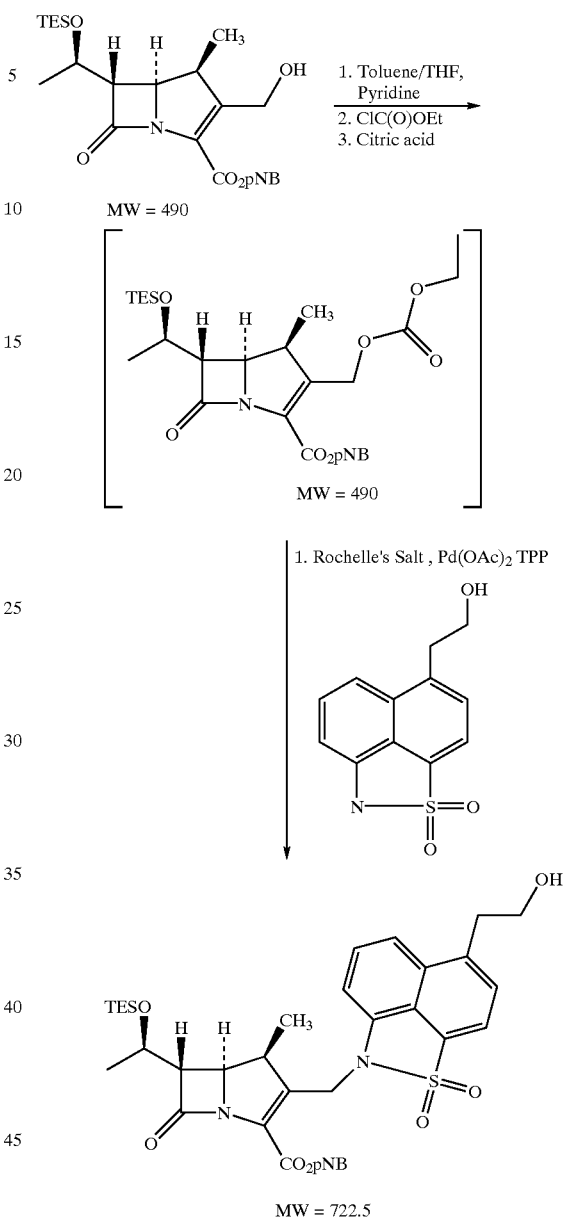

5 To a solution of the hydroxymethyl compound (1.65 Kg, 79 wt %, 2.66 mol) in toluene (12.5 L) at 25° C. under nitrogen was added THF (Kf-200 ugml-1, 4.2 L) and pyridine (815 mL, 10.1 mol). Ethylchloroformate (519 gms, 4.78 mol) was added over 40 minutes maintaining the reaction temperature at 20–28° C. The mixture was stirred at 25° C. for 1 h producing the carbonate (1.485 Kg).

To the carbonate solution was added hydroxyethylsultam (702 gms, 2.82 mol), palladium acetate (17.5 gms, 0.078 mol), triphenylphosphine (61.7 gms, 0.24 mol), and a 10% aqueous solution of potassium sodium tartrate in D.I. water (7.5 L). The resulting three phase mixture was warmed to reflux (80° C.) for 1 hour. The reaction mixture was cooled to 20° C. and filtered through solka flox plug (2" on a 6" scintered glass funnel). Toluene (3 L) was used to wash the

Example 2

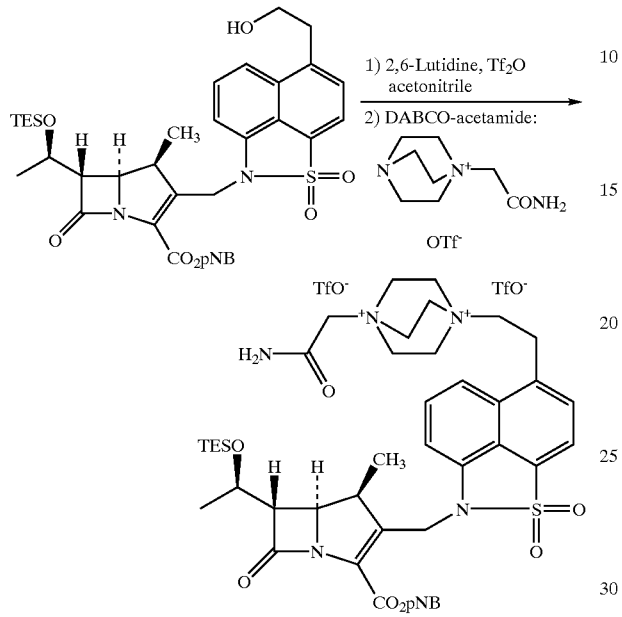

A solution of the product (coupled alcohol) (1650 g, 2.28 mol) from Example 1 in acetonitrile, [Kf<800 ug/mL, 5–15% toluene] (6.5 L), was charged into a 50 L flask. The flask was equipped with a N2 inlet, thermocouple, addition funnel and an overhead stirrer. 2,6-Lutidine (0.59 L, 5.02 mol (2.2eq)) was added within five minutes through the addition funnel. The solution was cooled to −25° C. to −30° C. and the triflic anhydride (0.42 L, 2.51 mol, (1.1 eq.)) was added slowly maintaining a temperature <−20° C. The reaction was deemed complete when <5A% starting material relative to triflate remained. DABCO acetamide triflate (764 g, 2.4 mol(1.05eq)) was charged and the solution warmed to 20° C. to 250° C. over 30 minutes and monitored by HPLC until all the triflate (<2A%) was converted to TES penultimate, about 2 hrs. at room temperature.

HPLC assay: Column, SB Phenyl 25 cm×4.6 mm, 210 nm detection, flow 1.5 mL/min, eluent A: aqueous H3PO4 (4 ml H3PO4 in 4 L H2O), eluent B: acetonitrile, gradient: 50% A to 10% over 15 min, then hold until 30 min. Retention times: 2,6-lutidine(1.4), TES penultimate (2.8), coupled methyl-naphthosultam (15.2), iodide (16.2), coupled alcohol (12.7), TPP (10.4).

The reaction was quenched by addition of water (0.41 L), followed by the addition of IPA (16 L) slowly over 1 hour. After 8 L of IPA was added the batch was seeded with 8 gm of TES penultimate. The solution was filtered through a coarse filter and washed with 8 L additional IPA to give 2.1 Kg of TES penultimate product.

Example 3

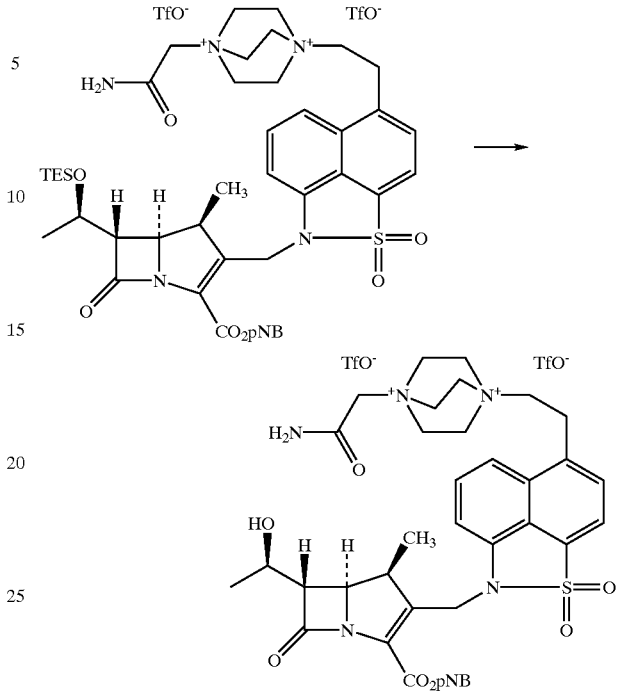

The TES penultimate (1 Kg) was slurried in 10 L IPA and then 200 mL 0.2N HCl was added. The reaction was monitored by HPLC until <1A% starting material was present. Another 10 L IPA was added slowly over 1 hour. The solution was then cooled to 3° C. and aged 30 minutes. The slurry was then filtered and washed with cold IPA (10 L) and dried in vacuo at 20° C. to give the penultimate.

HPLC conditions: Column: YMC-Sphere ODS-$H_{80}$ 25 cm×4.6 mm, Eluent B: aqueous KH2PO4(2.75 g KH2PO4 in 4 L $H_2O$), Eluent A: ACN, gradient: 10%A to 90%A over 15 min, hold 15 min, flow: 1.5 mL/min, detection: UV at 210 nm. Retention times: penultimate (8.2), DABCO adduct [-TES] (13.5(br)).

Example 4

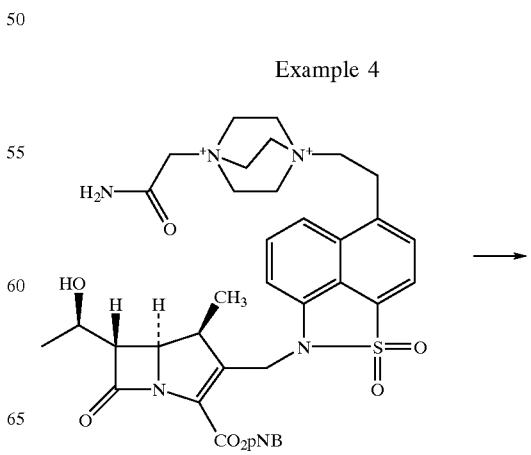

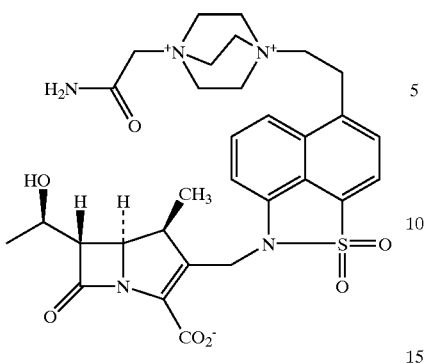

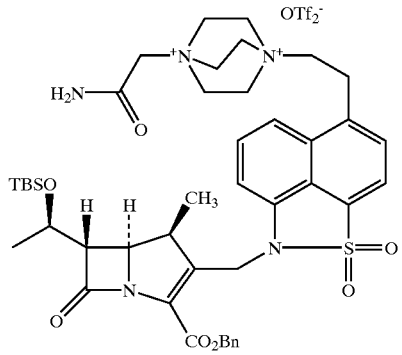

To an autoclave was added a mixture of 0.25M MOPS buffer (pH was adjusted to 7.1 with 50% NaOH; 345 mL), H$_2$O (200 mL), and THF (303 mL). The penultimate from Example 3 (64.5 wt % as free acid; 20 g; 17.0 mmol) was added to this mixture at room temperature. After stirring for 15 minutes at room temperature, 5 wt % palladium on carbon (3 g) was added and the catalyst was rinsed with H$_2$O (63 mL). IPA (303 mL) was added to the mixture. The reaction mixture underwent hydrogenolysis under 40 psi of hydrogen at room temperature for 1–2 hours. After the reaction was confirmed by HPLC (penultimate <0.1 mg/mL), the reaction mixture was immediately cooled down to 5° C. The catalyst was filtered off through a Solka-Floc bed (10 g) and rinsed with saturated aqueous sodium chloride (75 mL, three times). To the resulting filtrate was added sodium chloride (152 g) and the mixture was washed with iAmOH (500 mL; twice) and EtOAc (500 mL; twice). Isolation of the ultimate compound was obtained by column chromatography with polystylene resin (HP20s, Mitsubishi Chemical) and lyophilization.

A mixture of the isobutylcarbonate (6.0 g), sultam bis triflate (9.2 g) and lutidine (1.5 ml) were stirred in N-methylpyrrolidinone (30 ml). Palladium acetate (74 mg) and triethylphosphite (167 µl) were added and the mixture stirred at 30° C. for 20 h. Isopropanol (120 ml) was added and the resultant slurry aged at 5° C. for 1 h. Filtration gave the coupled product (14 g) which was recrystallized from acetonitrile/ethanol.

What is claimed is:

1. A process of synthesizing a carbapenem compound of formula 6:

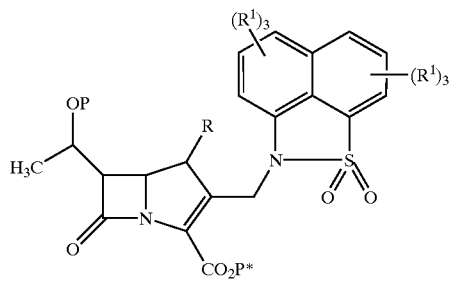

is disclosed wherein:

R represents H or methyl,

COOP* represents H, negative charge (which is balanced by a positively charged R' group or pharmaceutically acceptable counterion) or a carboxy protecting group;

P represents hydrogen, hydroxyl, or hydroxy-protecting group; and each R$^1$ is independently selected from: —R*; —Q; hydrogen; halo; —CN; —NO$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^h$; —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups, with the proviso that at least one R group contains a positive charge and no more than two positive charges are present on the molecule, said positive charge(s) balanced by a negatively charged counterion and/or P* when it is a negative charge;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{3-7}$ cycloalkyl, unsubstituted or substituted with one to four R$^d$ groups;

Example 5

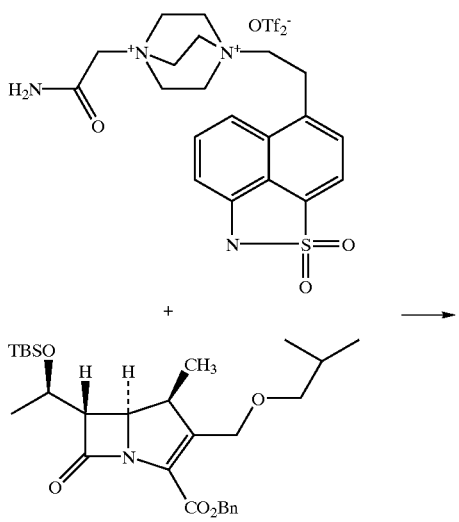

or $R^a$ and $R^b$ taken together with any intervening atoms represent a 4–6 membered saturated heterocyclic ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated heterocyclic ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —$R^*$ or —Q;

$R^e$, $R^f$ and $R^g$ represent hydrogen; —$R^*$; —$C_{16}$ straight- or branched-chain alkyl unsubstituted or substituted with one to four $R^i$ groups;

or $R^e$ and $R^f$ taken together with any intervening atoms represent a 4–6 membered saturated heterocyclic ring optionally interrupted by one to three of O, S, —C(O)—or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated heterocyclic ring, optionally interrupted by one or two of O, S, $SO_2$, —C(O)—, NH and $NCH_3$;

Q is selected from the group consisting of:

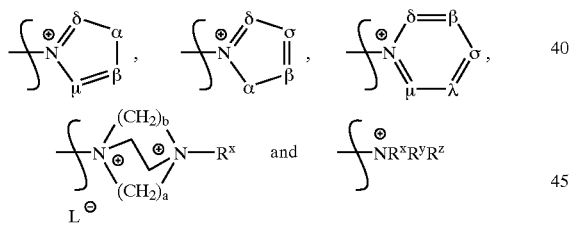

wherein:
a and b are 1, 2 or 3;
$L^-$ is a pharmaceutically acceptable counterion;
α represents O, S or $NR^s$;
β, δ, λ, μ and σ represent $CR^r$, N or $N^+R^s$, provided that no more than one of β, δ, λ, μ and σ is $N^+R^s$;
$R^*$ is selected from the group consisting of:

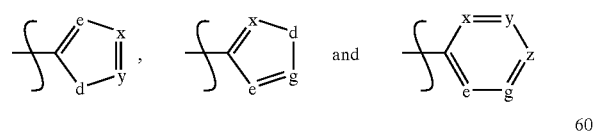

wherein:
d represents O, S or $NR^k$;
e, g, x, y and z represent $CR^m$, N or $N^+R^k$, provided that no more than one of e, g, x, y and z in any given structure represents $N^+R^k$;
$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR''R^o$; —$OR''$; —$SR''$; —$CONR''R^o$; —$COOR^h$; —$SOR''$; —$SO_2R''$; —$SO_2NR''R^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R''$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R''$ and $R^v$ represent hydrogen or —$C_{1-6}$ straight- or branched-chain alkyl, unsubstituted or substituted with one to four $R^i$ groups;

or $R''$ and $R^v$ together with any intervening atoms represent a 4–6 membered saturated heterocyclic ring optionally interrupted by one or more of O, S, NR w [w] or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four RI groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated heterocyclic ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$or —C(O)—;

or $R^x$ and $R^y$ together with any intervening atoms represent a 4–6 membered saturated heterocyclic ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered heterocyclic ring fused to the ring represented by $R^x$ and $R^y$ taken together, optionally interrupted by O, S, $NR^w$ or —C(O)—, said rings being unsubstituted or substituted with one to four $R^i$ groups;

comprising reacting a carbapenem of formula 4':

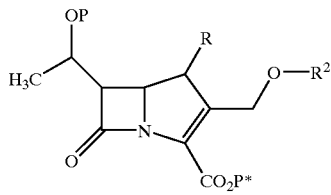

4' with a compound of formula 7:

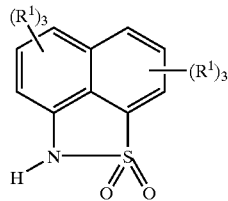

7 wherein R, $R^1$, P and P* are as previously defined and $R^2$ represents C(O)OR', C(O)R' or P(O)(OR")$_2$, wherein R' and R" independently represent $C_{1-6}$ alkyl, aryl or benzyl, in the presence of a palladium catalyst selected from the group consisting of $Pd(OAc)_2$, $Pd(PPh_3)_4$ $PdCl_2$, $PdCl_2(PPh_3)_2$, $PdCl_2(CH_3CN)_2$ or $Pd_2DBA$ (dibenzylidene acetone)$_3$, to produce a compound of formula 6.

2. A process in accordance with claim 1 wherein P represents a member selected from the group consisting of: trimethylsilyl (TMS), triethylsilyl (TES), t-butyldimethylsilyl (TBDMS), o-nitrobenzyloxycarbonyl, p-nitrobenzyloxycarbonyl, benzyloxycarbonyl, allyloxycarbonyl, t-butyloxycarbonyl and 2,2,2-trichloroethyloxycarbonyl.

3. A process in accordance with claim 1 wherein P* represents a member selected from the group consisting of: allyl, benzhydryl, 2-naphthylmethyl, benzyl, t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl, 4-pyridylmethyl and t-butyl.

4. A process according to claim 1 in which a base is optionally added and the temperature is about 0° C. to about 150° C.

5. A process according to claim 4 wherein the base is selected from the group consisting of triethylamine, trimethylamine, ethyldimethylamine, tri-n-propylamine, 1,8 diazabicyclo[5.4.0.]un-dec-7-ene (DBU), pyridine, lutidine, sodium carbonate, sodium bicarbonate, potassium bicarbonate, potassium carbonate, potassium sodium tartrate, potassium tartrate, potassium bitartrate, sodium tartrate, and sodium bitartrate.

6. A process according to claim 5 wherein the base is selected from the group consisting of pyridine, potassium sodium tartrate, sodium carbonate, sodium bicarbonate, potassium bicarbonate, and potassium carbonate.

7. A process in accordance with claim 1 wherein P is removed, when desired, by addition of an acid selected from the group consisting of HCl, $H_2SO_4$, MsOH (methane sulfonic acid), TFA (trifluoro acetic acid), $H_3PO_4$, TsOH (toluene sulfonic acid), TBAF (tetrabutylammonium fluoride), HF(hexafluoro)-pyridine, and ammonium bifluoride.

8. A process according to claim 1 wherein the palladium (Pd) catalyst further contains a ligand source selected from the group consisting of $AsPh_3$, trialkylphosphite, triarylphosphine, and DPPE (diphenylphosphino) ethane.

9. A process in accordance with claim 1 wherein P* is removed, when desired, by hydrogenolysis in the presence of palladium on carbon, Raney Nickel, $Pd(OH)_2$/carbon, palladium on $Al_2O_3$, platinum on carbon catalyst, or by reduction with a metal such as zinc or photolysis.

10. A process according to claim 8 wherein the palladium catalyst is $Pd(OAc)_2$ or $Pd_2DBA_3$, wherein DBA is dibenzylidene acetone.

11. A process according to claim 8 wherein the ligand source is $PPh_3$, trifurylphosphine, triethylphosphite, trimethylphosphite, tributylphosphite and tri-isopropylphosphite.

12. A process according to claim 11 which is conducted at a temperature of about 20° C. to about 35° C. and $R^1$ of compound 7 is a charged substituent incorporated before reaction with compound 4'.

13. A process according to claim 8 wherein the catalysts system represents $Pd(OAc)_2/P(OR^+)_3$, $Pd_2(DBA)_3/P(OR^+)_3$, $Pd(OAc)_2$/Triarylphosphine, or $Pd_2(DBA)_3$/Triarylphosphine, wherein $R^+$ is $C_{1-10}$ alkyl.

14. A process according to claim 13 which is conducted at a temperature of about 20° C. to about 35° C. and $R^i$ of compound 7 is a charged substituent.

15. A process according to claim 13 wherein the catalyst system represents $Pd(OAc)_2$/TPP, $Pd_2(DBA)_3$/TPP, $Pd(OAc)_2$/Triethylphosphite, $Pd_2(DBA)_3$/Triethylphosphite, $Pd(OAC)_2$/trimethylphosphite, $Pd_2(DBA)_3$/trimethylphosphite, $Pd(OAc)_2$/tributylphosphite, $Pd_2(DBA)_3$/tributylphosphite, $Pd(OAc)_2$/tri-isopropylphosphite, or $Pd_2(DBA)_3$/tri-isopropylphosphite, wherein DBA means dibenzylidene acetone and TPP means triphenylphosphite.

16. A process according to claim 15 which is conducted at a temperature of about 20° C. to about 35° C. and R' of compound 7 is a charged substituent.

17. A process according to claim 1 wherein R represents methyl.

18. A process for making a compound of formula 6:

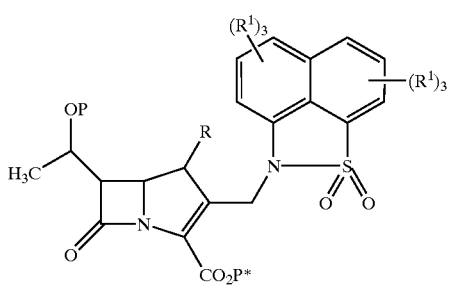

6 is disclosed wherein:

R represents H or methyl,

COOP* represents a carboxylic acid, a carboxylate anion (which is balanced by a positively charged $R^1$ group or pharmaceutically acceptable counterion), or a carboxylic acid protected by a protecting group;

P represents hydrogen, hydroxyl, or hydroxy-protecting group; and each $R^1$ is independently selected from: —R*; —Q; hydrogen; halo; —CN; —NO$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^h$; —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups, with the proviso that at least one R$^1$ group contains a positive charge and no more than two positive charges are present on the molecule, said positive charge(s) balanced by a negatively charged counterion and/or P* when it is a negative charge;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{3-7}$ cycloalkyl, unsubstituted or substituted with one to four R$^d$ groups;

or R$^a$ and R$^b$ taken together with any intervening atoms represent a 4–6 membered saturated heterocyclic ring optionally interrupted by one or more of O, S, NR$^c$, with R$^c$ as defined above, or —C(O)—, said ring being unsubstituted or substituted with one to four R$^i$ groups;

or R$^b$ and R$^c$ taken together with any intervening atoms represent a 4–6 membered saturated heterocyclic ring optionally interrupted by one to three of O, S, NR$^a$, with R$^a$ as defined above, or —C(O)—, said ring being unsubstituted or substituted with one to four R$^i$ groups;

each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$CONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —R*; —C$_{1-6}$ straight- or branched-chain alkyl unsubstituted or substituted with one to four R$^i$ groups;

or R$^e$ and R$^f$ taken together with any intervening atoms represent a 4–6 membered saturated heterocyclic ring optionally interrupted by one to three of O, S, —C(O)— or NR$^g$ with R$^g$ as defined above, said ring being unsubstituted or substituted with one to four R$^i$ groups;

each R$^i$ independently represents halo; —CN; —NO$_2$; phenyl; —NHSO$_2$R$^h$; —OR$^h$; —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

each R$^h$ independently represents hydrogen, a —C$_{1-6}$ straight or branched-chain alkyl group, a —C$_3$–C$_6$ cycloalkyl group or phenyl, or when two R$^h$ groups are present, said R$^h$ groups may be taken in combination and represent a 4–6 membered saturated [carbon] heterocyclic ring, optionally interrupted by one or two of O, S, SO$_2$, —C(O)—, NH and NCH$_3$;

Q is selected from the group consisting of:

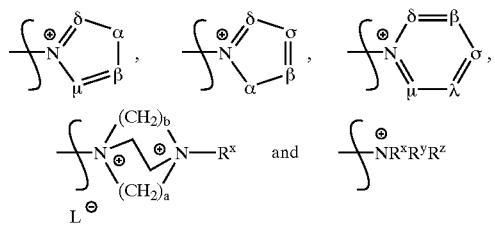

wherein:
a and b are 1, 2 or 3;
L$^-$ is a pharmaceutically acceptable counterion;
α represents O, S or NR$^s$;
β, δ, λ, μ and σ represent CR$^t$, N or N$^+$R$^s$, provided that no more than one of β, δ, λ, μ and σ is N$^+$R$^s$;
R* is selected from the group consisting of:

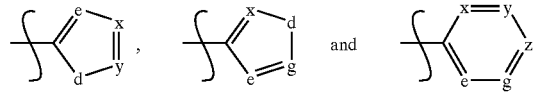

wherein:
d represents O, S or NR$^k$;
e, g, x, y and z represent CR$^m$, N or N$^+$R$^k$, provided that no more than one of e, g, x, y and z in any given structure represents N$^+$R$^k$;
R$^k$ represents hydrogen; —C$_{1-6}$ straight- or branched-chain alkyl, unsubstituted or substituted with one to four R$^i$ groups; or —(CH$_2$)$_n$Q where n=1, 2 or 3 and Q is as previously defined;

each R$^m$ independently represents a member selected from the group consisting of: hydrogen; halo; —CN; —NO$_2$;—NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$;—NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; and —(CH$_2$)$_n$Q where n and Q are as defined above;

R$^n$ and R$^o$ represent hydrogen, phenyl; —C$_{1-6}$ straight- or branched-chain alkyl unsubstituted or substituted with one to four R$^i$ groups;

each R$^s$ independently represents hydrogen; phenyl or —C$_{1-6}$ straight- or branched-chain alkyl, unsubstituted or substituted with one to four R$^i$ groups;

each R$^t$ independently represents hydrogen; halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

or R$^u$ and R$^v$ together with any intervening atoms represent a 4–6 membered saturated heterocyclic ring optionally interrupted by one or more of O, S, NR$^w$ or —C(O)—, said ring being unsubstituted or substituted with one to four R$^i$ groups;

each R$^w$ independently represents hydrogen; —C$_{1-6}$ straight- or branched-chain alkyl, unsubstituted or substituted with one to four R$^i$ groups; C$_{3-6}$ cycloalkyl optionally substituted with one to four R$^i$ groups; phenyl optionally substituted with one to four R$^i$ groups, or heteroaryl optionally substituted with 1–4 R$^i$ groups;

or R$^h$ and R$^w$ taken together with any intervening atoms represent a 5–6 membered saturated heterocyclic ring, optionally interrupted by one or two of O, S, SO$_2$, NH or NCH$_3$;

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R$^y$ and R$^z$ represent hydrogen; phenyl; —C$_{1-6}$ straight or branched chain alkyl, unsubstituted or substituted with one to four R$^i$ groups, and optionally interrupted by O, S, NR$^w$, N$^+$R$^h$R$^w$or —C(O)—;

or R$^x$ and R$^y$ together with any intervening atoms represent a 4–6 membered saturated heterocyclic ring optionally interrupted by O, S, SO$_2$, NR$^w$, N$^+$R$^h$R$^w$or —C(O)—, unsubstituted or substituted with 1–4 R$^i$ groups, and when R$^x$ and R$^y$ together represent a 4–6 membered ring as defined above, R$^z$ is as defined above or R$^z$ represents an additional saturated 4–6 membered heterocyclic ring fused to the ring represented by R$^x$ and R$^y$ taken together, optionally interrupted by O, S, NR$^w$ or —C(O)—, said rings being unsubstituted or substituted with one to four R$^i$ groups;

comprising,

Step 1.

reacting a carbapenem of formula 3:

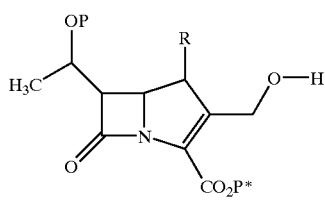

3 with an alkylhaloformate in the presence of a base to produce a compound of formula 4':

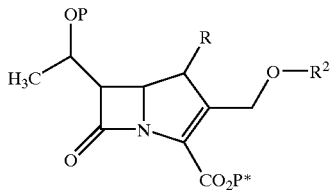

4'

Step 2.
reacting 41 with a compound of formula 7:

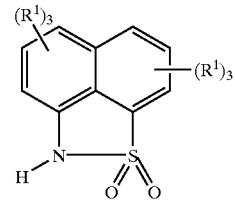

7 wherein R, R$^1$, P and P* are as previously defined and R$^2$ represents C(O)OR', wherein R' and R", independently represent C$_{1-6}$ alkyl in the presence of a palladium (Pd) catalyst selected from the group consisting of Pd(OAc)$_2$, Pd(PPh$_3$)$_4$PdCl$_2$, PdCl$_2$(PPh$_3$)$_2$, PdCl$_2$(CH$_3$CN)$_2$ or Pd$_2$DBA(dibenzylidene acetone)$_3$, to produce a compound of formula 6.

19. A process according to claim 1 wherein R$^2$ represents C(O)OR' or P(O)(OR")$_2$.

20. A process in accordance with claim 1 wherein R, P and P* are as previously described and one R$^1$ group represents a —C$_{1-6}$ straight or branched chain alkyl group, substituted with one to four R$^d$ groups, wherein one R$^d$ group represents —R* or Q.

21. A process of synthesizing a carbapenem compound of formula 6:

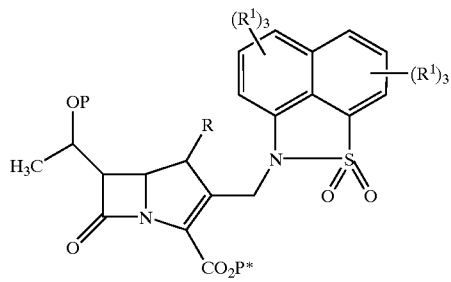

6 is disclosed wherein:

R represents H or methyl,

COOP* represents a carboxylic acid, a carboxylate anion (which is balanced by a positively charged R$^1$ group or pharmaceutically acceptable counterion) or a carboxylic acid protected by a protecting group;

P represents hydrogen, hydroxyl, or hydroxyl protected by a hydroxyl-protecting group; and one R$^1$ group represents a —C$_{1-6}$ straight or branched chain alkyl group, substituted with one to four R$^d$ groups, wherein one R$^d$ group represents —R* or Q and the remaining R$^1$ groups are hydrogen with the proviso that at least one R$^1$ group represents a positive charge and no more than two positive charges are present on the molecule, said positive charge(s) balanced by a negatively charged counterion and/or P* when it is a negative charge;

each $R^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamirnidoyl or ureido;

each $R^h$ independently represents hydrogen, a —C$_{1-6}$ straight or branched-chain alkyl group, a —C$_3$–C$_6$ cycloalkyl group or phenyl, or when two R$^h$ groups are present; said R$^h$ groups may be taken in combination and represent a 4–6 membered saturated heterocyclic ring, optionally interrupted by one or two of O, S, SO$_2$, —C(O)—, NH and NCH$_3$;

Q is selected from the group consisting of:

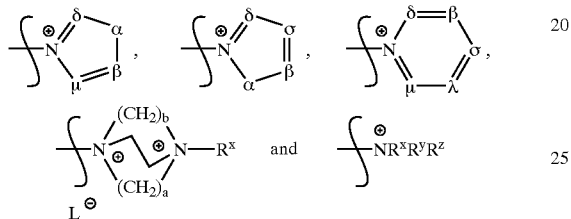

wherein:
a and b are 1, 2 or 3;
L$^-$ is a pharmaceutically acceptable counterion;
α represents O, S or NR$^s$;
β, δ, λ, μ and σ represent CR$^r$, N or N$^+$R$^s$, provided that no more than one of β, δ, λ, μ and σ is N$^+$R$^s$;
R* is selected from the group consisting of:

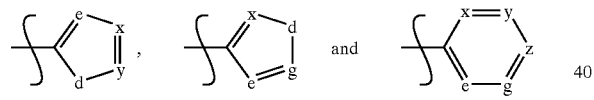

wherein:
d represents O, S or NR$^k$;
e, g, x, y and z represent CR$^m$, N or N$^+$R$^k$, provided that no more than one of e, g, x, y and z in any given structure represents N$^+$R$^k$;
R$^k$ represents hydrogen; —C$_{1-6}$ straight- or branched-chain alkyl, unsubstituted or substituted with one to four R$^i$ groups; or —(CH$_2$)$_n$Q where n=1, 2 or 3 and Q is as previously defined;
each R$^m$ independently represents a member selected from the group consisting of: hydrogen; halo; —CN; —NO$_2$; —NR$^n$R$^o$; —OR$^n$; —SR$^n$; —CONR$^n$R$^o$; COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$; —NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; and —(CH$_2$)$_n$Q where n and Q are as defined above;
R$^n$ and R$^o$ represent hydrogen, phenyl; —C$_{1-6}$ straight- or branched-chain alkyl unsubstituted or substituted with one to four R$^i$ groups;

each R$^s$ independently represents hydrogen; phenyl or —C$_{1-6}$ straight- or branched-chain alkyl, unsubstituted or substituted with one to four R$^i$ groups;

each R$^t$ independently represents hydrogen; halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

or R$^u$ and R$^v$ together with any intervening atoms represent a 4–6 membered saturated heterocyclic ring optionally interrupted by one or more of O, S, NR$^w$ or —C(O)—, said ring being unsubstituted or substituted with one to four R$^i$ groups;

each R$^w$ independently represents hydrogen; —C$_{1-6}$ straight- or branched-chain alkyl, unsubstituted or substituted with one to four R$^i$ groups; C$_{3-6}$ cycloalkyl optionally substituted with one to four R$^i$ groups; phenyl optionally substituted with one to four R$^i$ groups, or heteroaryl optionally substituted with 1–4 R$^i$ groups;

or R$^h$ and R$^w$ taken together with any intervening atoms represent a 5–6 membered saturated heterocyclic ring optionally interrupted by one or two of O, S, SO$_2$, NH, or NCH$_3$;

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one , to two C$_{1-3}$ straight- or branched-chain alkyl groups, said alkyl groups being unsubstituted or substituted with one to four R$^i$ groups;

R$^y$ and R$^z$ represent hydrogen; phenyl; —C$_{1-6}$ straight or branched chain alkyl, unsubstituted or substituted with one to four R$^i$ groups, and optionally interrupted by O, S, NR$^w$, N$^+$R$^h$R$^w$ or —C(O)—;

or R$^x$ and R$^y$ together with any intervening atoms represent a 4–6 membered saturated heterocyclic ring optionally interrupted by O, S, SO$_2$, NR$^w$, N$^+$R$^h$R$^w$ or —C(O)—, unsubstituted or substituted with 1–4 R$^i$ groups, and when R$^x$ and R$^y$ together represent a 4–6 membered ring as defined above, R$^z$ is as defined above or R$^z$ represents an additional saturated 4–6 membered heterocyclic ring fused to the ring represented by R$^x$ and R$^y$ taken together, optionally interrupted by O, S, NR$^w$ or —C(O)—, said rings being unsubstituted or substituted with one to four R$^i$ groups;

comprising reacting a carbapenem of formula 4':

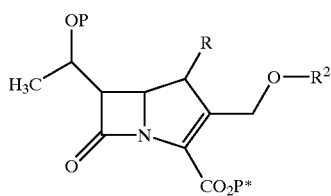
4' with a compound of formula 7:

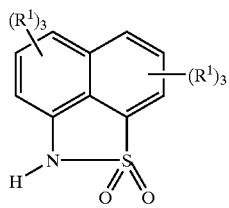
7 wherein R, $R^1$, P and P* are as previously defined and $R^2$ represents C(O)OR' or P(O)(OR")$_2$, R' and R" independently represent $C_{1-6}$ alkyl, benzyl or aryl, in the presence of a catalyst selected from the group consisting of Pd(OAc)$_2$/TPP(triphenylphosphite), Pd$_2$(DBA-dibenzylidene acetone)$_3$/TPP(triphenylphosphite), Pd(OAc)$_2$/Triethylphosphite, Pd$_2$(DBA-dibenzylidene acetone)$_3$/Triethylphosphite, Pd(OAc)$_2$/trimethylphosphite, Pd$_2$(DBA-dibenzylidene acetone)$_3$/trimethylphosphite, Pd(OAc)$_2$/tributylphosphite, Pd$_2$(DBA-dibenzylidene acetone)$_3$/tributylphosphite, Pd(OAc)$_2$/tri-isopropylphosphite, Pd$_2$(DBA-dibenzylidene acetone)$_3$/tri-isopropylphosphite, and Pd(OAc)$_2$/trifurylphosphine to produce a compound of formula 6.

22. A process in accordance with claim 21 in which a base is optionally added, said base selected from the group consisting of pyridine, potassium sodium tartrate, sodium carbonate, sodium bicarbonate, potassium bicarbonate, and potassium carbonate.

23. A process according to claim 21 which is conducted at a temperature of about 20° C. to about 35° C. and $R^1$ of compound 7 is a charged substituent.

24. A process in accordance with claim 21 wherein P* represents a member selected from the group consisting of: allyl, benzhydryl, 2-naphthylmethyl, benzyl, t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl, 4-pyridylmethyl and t-butyl.

25. A process according to claim 18 in which a base is optionally added in step 2.

26. A process according to claim 18 where the alkylhaloformate is isobutylchloroformate, ethylchloroformate, methylchoroformate, propylchloroformate.

27. A process according to claim 25 wherein the base in steps 1 and 2 are independently selected from the group consisting of triethylamine, trimethylamine, ethyldimethylamine, tri-n-propylamine, 1,8 diazabicyclo [5.4.0.]un-dec-7-ene (DBU), pyridine, lutidine, sodium carbonate, sodium bicarbonate, potassium bicarbonate, potassium carbonate, potassium sodium tartrate, potassium tartrate, potassium bitartrate, sodium tartrate, and sodium bitartrate, and the palladium catalyst further contains a ligand source, wherein the palladium source is Pd(OAc)$_2$, Pd(PPh$_3$)$_4$PdCl$_2$, PdCl$_2$(PPh$_3$)$_2$, PdCl$_2$(CH$_3$CN)$_2$ or Pd$_2$DBA$_3$, and the ligand source is AsPh$_3$, trialkylphosphite, triarylphosphine, and DPPE (diphenylphosphino) wherein DBA means dibenzylidene acetone.

* * * * *